(12) United States Patent
Weiss

(10) Patent No.: US 9,140,665 B2
(45) Date of Patent: Sep. 22, 2015

(54) METHOD FOR AN OPERATIONAL TEST MEASUREMENT OF A LAMBDA PROBE, AND DEVICE FOR CARRYING OUT METHOD

(75) Inventor: Tobias Weiss, Herbertingen (DE)

(73) Assignee: MTU Friedrichshafen GmbH, Friedrichshafen (DE)

(*) Notice: Subject to any disclaimer, the term of this patent is extended or adjusted under 35 U.S.C. 154(b) by 303 days.

(21) Appl. No.: 13/607,176

(22) Filed: Sep. 7, 2012

(65) Prior Publication Data
US 2013/0055786 A1 Mar. 7, 2013

(30) Foreign Application Priority Data
Sep. 7, 2011 (DE) .................. 10 2011 082 293

(51) Int. Cl.
*G01N 27/00* (2006.01)
*G01N 27/417* (2006.01)

(52) U.S. Cl.
CPC .................. *G01N 27/4175* (2013.01)

(58) Field of Classification Search
CPC .......... G01N 33/0006; G01N 27/4163; G01N 27/4175; G01N 33/007
USPC ........................................................ 73/1.07
See application file for complete search history.

(56) References Cited

U.S. PATENT DOCUMENTS

| | | | |
|---|---|---|---|
| 4,092,852 A * | 6/1978 | Fowler et al. | 73/114.69 |
| 5,137,616 A * | 8/1992 | Poor et al. | 204/428 |
| 5,211,820 A * | 5/1993 | Poor et al. | 205/784.5 |
| 7,473,340 B2 * | 1/2009 | Bolz | 204/406 |
| 7,584,642 B2 | 9/2009 | Michalske et al. | |

FOREIGN PATENT DOCUMENTS

| | | |
|---|---|---|
| DE | 19637726 A1 | 3/1998 |
| DE | 102005056152 A1 | 5/2007 |
| DE | 10 2008 046 121 A1 | 3/2010 |

OTHER PUBLICATIONS

Wikipedia—Web page Http://en.wikipedia.org/wiki/Oxygen_sensor. Sep. 7, 2012.

* cited by examiner

*Primary Examiner* — Hezron E Williams
*Assistant Examiner* — Rodney T Frank
(74) *Attorney, Agent, or Firm* — Fishman Stewart Yamaguchi PLLC

(57) ABSTRACT

A method for the operational test measurement of a lambda probe, particularly for the purpose of calibrating and/or determining the status of the lambda probe, wherein pure air is circulated around a probe head of the lambda probe is disclosed. The method has the following steps:, —insertion of the lambda probe into a flow receptacle which is separate from an engine construction, in such a manner that an air stream (L) can be circulated around the probe head; generation of an air stream (L) in the flow receptacle; evaluation of probe measurement signals (S), wherein a calibration value is obtained and/or a heating current of the lambda probe is evaluated. A device for carrying out the method, as well as a system, is also disclosed herein.

14 Claims, 2 Drawing Sheets

METHOD FOR AN OPERATIONAL TEST MEASUREMENT OF A LAMBDA PROBE, AND DEVICE FOR CARRYING OUT METHOD

CROSS REFERENCE TO RELATED APPLICATIONS

This application is a National Phase Application which application claims priority to DE 10 2011 082 293.3 filed on Sep. 7, 2011, which application is incorporated herein by reference in its entirety.

TECHNICAL FIELD

The disclosure relates to a method for an operational test measurement of a lambda probe, wherein pure air is circulated around a probe head of the lambda probe. In addition, the disclosure relates to a device for carrying out such a method. The disclosure also relates to a system of such a device having a lambda probe.

BACKGROUND

In general, a lambda probe functions as a device for measuring a gas concentration in an exhaust stream, as part of the design of an internal combustion engine—termed "engine design" below. By means of the measurement result, the so-called lambda ratio of combustion air to fuel, or fuel to exhaust gas, is determined and may be utilized to control the combustion of fuel. A lambda sensor can be implemented as a lambda probe, for example, or—for the purpose of determining the $NO_x$ fraction in a gas mixture—can be implemented as a $NO_x$ probe. In addition, sensors used to determine the concentration of other gases, for example $NH_3$, CO, or HC can be contemplated, and are termed "lambda probes" in general in the following text.

A correct lambda ratio, or a $NO_x$ concentration, or the other concentration values named above which are part of the detection by the lambda probe, are important parameters for the control of the combustion in the combustion chamber of an internal combustion engine, and for enabling adequate exhaust scrubbing by a catalytic converter.

A lambda probe generally has a probe head which is formed as a ceramic measuring element, wherein the same is capable of measuring a gas property, as explained above—generally via a probe voltage. For example, the ceramic measuring element can be realized by means of a concentration cell (Nernst cell), preferably based on an yttrium-doped zirconium dioxide ceramic. The ceramic measuring element can also be realized with a resistance cell (Arrhenius cell), for example with a semi-conducting titanium dioxide ceramic. The measurement result is obtained as the result of ionic conduction by oxygen and/or oxygen occupying a lattice void in the ceramic, according to the measuring principle, with a resulting probe voltage or probe current. Such a probe signal can be a measurement of a difference in concentration between a reference gas and a measured gas (Nernst cell) as the result of a partial pressure difference, or a conductance between a reference gas compartment and a measured gas compartment (Arrhenius cell). For this purpose, the measuring element is regularly heated to temperatures above 650° C., or in some cases—if a YSZ ceramic is used—to temperatures above 300° C.

For example, a discrete-level sensor provides a lambda value which is equal to 1 and a probe voltage between approximately 200 and 800 mV (optimally approx. 450 mV), a lambda value larger than 1 (lean mixture with too much air) at a voltage less than 200 mV, and a lambda value smaller than 1 (rich mixture with too much fuel) at voltages over 800 mV. A discrete-level sensor is characterized in that the characteristic curve is extremely steep in a very narrow intermediate range on either side of lambda=1, meaning between 200 and 800 mV—the so-called lambda window. In this range, the voltage changes, almost in a jump, in dependence on the air-fuel ratio.

In contrast, a wide-band probe is characterized by a suitable layered construction of a pump cell of a measuring gap, and of a Nernst cell, for example. An exhaust gas flow is on one side of the pump cell. An air flow is on the other side of the Nernst cell. The pump cell connects the measuring gap to the exhaust stream via a diffusion channel. The measured gas is constantly held at lambda=1 in the measuring gap via the diffusion channel. The pump current provides information on the lambda ratio in the exhaust gas flow. In the case of a wide-band probe, it is important for the measurement result that the probe is heated.

In general, then, it can be said that lambda probes indirectly measures the current prevailing oxygen concentration in the gaseous medium which surrounds them. The electrical pump current needed for the measuring method—for example, in the case of wide-band probes—is measured and converted via a stored characteristic curve. The precision of this measurement also significantly depends on the calibration interval because—as explained—potentially steep ramps in the probe signal must be taken into consideration as part of the measurement result.

The method of leaving a lambda probe in an engine construction and circulating air around the same for the purpose of determining the probe status is known. For example, the internet document http://de.wikibooks.org/wiki/Mb-Technik/_M07-KE/_Lambda-Sonde explains how it is possible to check the status of a lambda probe as regards to heat generation, the probe voltage signal, or lag smearing of the probe. For this purpose, probe signals or a heating current are measured when the engine is running and at operating temperature.

For the purpose of calibration, the method of circulating pure air around a probe head of the lambda probe is known. In general, boundary conditions of the manufacturer which are suited to such calibration must be observed. A calibration factor can generally be determined by means of analysis software provided by the manufacturer, or ECU software, or suitable evaluation devices—also known as lambdameters—for example. For example, the INCA diagnosis and calibration tool from the Bosch company or the LA4 or AWS2 lambdameter from the ETAS company are known. In general, such calibration or status determination methods are suitable for the LSU or LSU ADV probe from the Bosch company.

A problem with all methods currently known for the calibration of a lambda probe is that the lambda probe remains in the engine construction. It is also a problem that a true calibration of the lambda probe can only take place if it is reasonably correct to assume that the lambda probe is intact; however, if the lambda probe is in a malfunctioning state, a calibration of the same only makes a limited amount of sense.

It would be desirable for the operational test measurement to be able to not only calibrate a lambda probe but also determine the status thereof. It is also desirable to be able to perform an operational test measurement of the lambda probe independently of influences from the engine.

SUMMARY

The disclosure addresses of the need of enabling an operational test measurement of a lambda probe which complies with calibration-specific boundary conditions but is nevertheless independent of engine effects, and which moreover is capable of providing both a status of the lambda probe and a calibration thereof.

According to the disclosure, a probe is inserted in a flow receptacle which is separate from an engine construction, in such a manner that an air flow can be circulated around a probe head of the probe. On the one hand, this approach ensures that the lambda probe is measured independently of engine effects. On the other hand, the fact that a pure air stream can be circulated around the probe ensures that it is possible to comply with conventional boundary conditions, such as those for regular operation of the probe, including surrounding temperature, pressure, moisture, etc., for example. The operational test measurement is realized with the circulation of pure air around the probe, corresponding to a lambda ratio of infinity.

In addition, according to the disclosure, an air stream is generated in the flow receptacle. An air stream is preferably generated which has a flow speed with a lower threshold of 1 m/s. In this way, the risk of oxidation of $N_2$ and $O_2$ from the surrounding air is largely ruled out. The flow speed is preferably set below 80 m/s. In this way, the risk of the sensor cooling off as a result of the transfer of heat to the air is largely ruled out.

In addition, according to the disclosure, an evaluation of probe signals is carried out when the air stream is generated, wherein a calibration value is determined and/or a heating current of the lambda probe is evaluated. The calibration process can be initiated by an activation of a start controller in the ECU software or a suitable evaluation unit, for example. A suitable diagnosis and calibration tool, such as INCA, for example, can generate a calibration factor via suitable software, wherein this calibration factor serves as the calibration value for a characteristic probe curve. Following regular calibrations, the calibration factor is then applied according to the stored sensor and gas properties. The characteristic probe curve can be scaled via a correction factor determined by means of the calibration, for example. Particularly in a steep region of a probe voltage (for a discrete-level probe) or a pump current (for a wide-band probe), a lambda value output by the lambda sensor is decisively proportional to the scaling of the characteristic sensor curve. The disclosure contemplates that precision can vary within a range of up to 17%. The disclosure arrangement is based on the realization that it should be possible in principle to calibrate the lambda probe independently of engine effects, with both a calibration and a status determination, via the heating current of the lambda probe using the concept underlying the disclosure.

A device is also disclosed, having a flow receptacle with a support which receives a lambda probe in such a manner that an air flow can be circulated around a probe head of the lambda probe. In addition, the device includes an evaluation unit for evaluating probe measurement signals, and obtaining a calibration value.

According to the disclosure, the device also has a vacuum device which can be connected to the flow receptacle for the purpose of generating an air stream in the flow receptacle, wherein the vacuum device is designed in the form of a vacuum cleaner. By means of the design of the vacuum device as a vacuum cleaner, a constructive solution is advantageously found which is comparatively technically simple, and which is available not only where there is an engine test bench, but also in the field as well. As a result, the device can be used worldwide at any location, for example as a tool in the customer service industry, or as part of development activities in the field.

In addition, the flow receptacle is provided separately from an engine. The flow receptacle provided separately from an engine fundamentally enables a status determination and calibration of a lambda probe independently of engine effects.

The flow receptacle also advantageously offers all the prerequisites for enabling the specifications required for a reproducible measurement and a standardized probe receiver. As such, the device can be used independently of any specific test bench and engine.

In addition, according to the disclosure, the evaluation device is designed to evaluate a heating current of the lambda probe. Because lambda probes play a very important role for the coming emission requirements, the status determination, combined with a calibration, is of increasing importance because the emissions of the engine depend significantly on a lambda ratio output by the lambda probe. As such, it is possible by means of the concept of the disclosure to thoroughly check whether an engine behavior which deviates from the standard is due to the probe or to the engine.

The concept disclosed herein has proven particularly preferred for a system consisting of a wide-band lambda probe and the device described above.

Advantageous exemplary implementations of the disclosure are found in the dependent claims, and provide specific advantageous possibilities for realizing the concept explained above in the framework of the problem addressed by the disclosure, as well as further advantages.

It has proven particularly preferred to carry out the calibration and status determination of the lambda probe at the same time. For example, a heating current of the lambda probe can be used in one exemplary arrangement as an indicator for adequate flow speed during the calibration. As such, this measure ensures that the correct boundary conditions are present during the calibration.

In one exemplary arrangement, the heating current of the lambda probe is utilized to carry out a status determination of the lambda probe. The heating current of the lambda probe can particularly be used as an indicator for a malfunction of the lambda probe.

In addition, it has proven particularly advantageous that, for the purpose of evaluating the heating current, a heating current experience range is established, and also that it is determined whether the measured heating current is within the heating current experience range.

For carrying out the calibration method, it has proven advantageous that an air stream is generated in the flow receptacle by means of:

attaching the flow receptacle to a vacuum device;
activating the vacuum device, such that an air flow circulates around the probe head.

The probe may be supplied with current, and probe start signals are preferably detected prior to the generation of an air stream. This has the advantage that, with the startup of the air stream, the tracking of the development of the calibration value is possible, in contrast to stationary air.

In addition, the method also offers the possibility—also for observing preferred boundary conditions—of feeding probe signals via a wiring harness, for example a vehicle wiring harness. As such, no separate wiring is necessary for the lambda probe. In addition or as an alternative thereto, probe signals are detected via an engine control device and/or a separate evaluation device connected to the wiring harness, and evaluated. The evaluation by standardized logical and diagnostic software advantageously enables an immediate, local statement about the probe status.

A vacuum cleaner has proven a particularly preferred example as the vacuum device for carrying out the method. As such, the method has a high degree of flexibility for the user.

The flow receptacle may be designed in the form of a tube. This results in preferred flow conditions during the calibration. The tube particularly has a cylindrical crosssection. A steel tube has proven particularly preferred. In this way, it is preferably possible to meet the installation specifications for the lambda probe when calibrating the same.

The flow receptacle is connected to a vacuum socket of the vacuum cleaner via a flexible adapter. As such, it is possible to establish compatibility between the flow receptacle and the vacuum cleaner at virtually any location on earth. As such, it is particularly possible to adapt a diameter of the flow receptacle to the diameter of a vacuum socket of the vacuum cleaner.

Embodiments of the disclosure are described below with reference to the drawing. The drawing is not necessarily intended to thoroughly illustrate all possible embodiments. Rather, the illustration is given in schematic and/or slightly distorted form where expedient for the explanation. Readers are directed to the relevant prior art for designs additional to the teaching which is directly recognizable in the drawing. It should be noted at this point that numerous modifications and alterations can be made concerning the form and details of any embodiment without deviating from the general idea of the disclosure. The features of the disclosure disclosed in the description, in the drawing, and in the claims can be essential to the implementation of the disclosure both individually and in any combination thereof. In addition, all combinations of at least two features described in the description, the drawing, and/or the claims fall within the scope of the disclosure. The general idea of the disclosure is not restricted to the exact form or the details of the preferred embodiments illustrated and described below, nor to a subject matter which would be restricted compared to the subject matter claimed in the claims. Where measurement ranges are given, values lying inside the named limits are also disclosed as threshold values, and can be used and claimed in any corresponding manner. For reasons of simplicity, the same reference numbers are used below for identical or similar parts, or parts with identical or similar functions.

BRIEF DESCRIPTION OF THE DRAWINGS

Additional advantages, features, and details of the disclosure are found in the following description of the preferred embodiments and with reference to the illustration, wherein.

DETAILED DESCRIPTION

Figure 1:
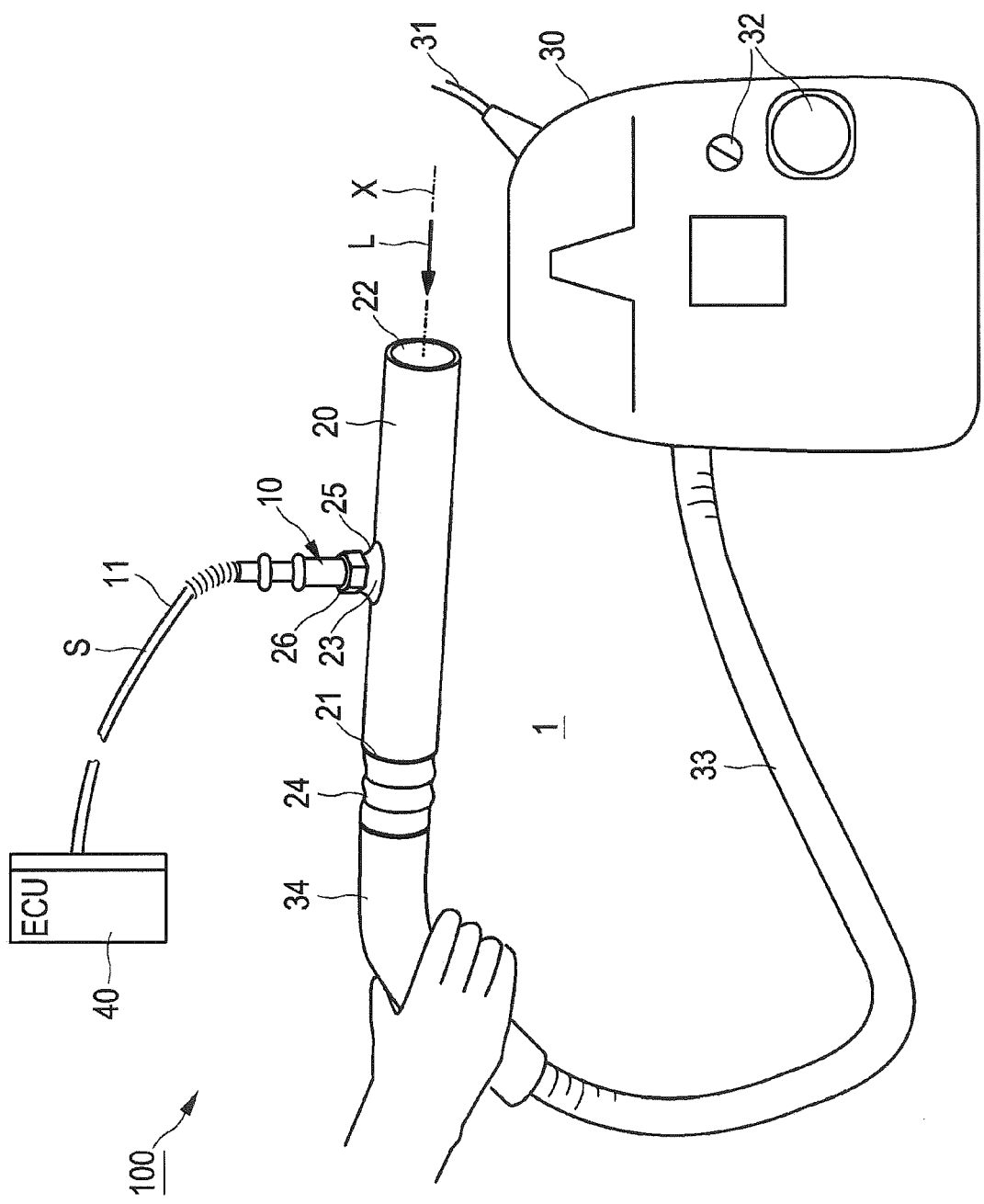
FIG. 1 shows a schematic illustration of a calibration device having a wide-band lambda probe for carrying out a calibration method of the wide-band lambda probe according to an exemplary embodiment.

FIG. 1 shows a system 100 for calibrating a lambda probe 10 with a suitable calibration device 1. The calibration device 1 also has a flow receptacle 20 in the form of a steel tube, a vacuum cleaner 30, and an evaluation device 40 which in the present case is in the form of a central engine control unit ECU. The vacuum cleaner 30 may be a conventional vacuum cleaner which can be connected to every conventional electrical network via a normal electric connector 31 and operated. The vacuum cleaner has corresponding controllers 32 to adjust its vacuum strength, such that a flow speed in a vacuum line 33 of the vacuum cleaner can be adjusted. The vacuum line 33 opens into a vacuum socket 34 which must be held by hand by the user in a suitable manner. The flow receptacle 20 in the present case is designed in the form of a steel tube which is connected to the vacuum socket 34 of the vacuum cleaner 30 via a flexible adapter 24 made of rubber. It is possible to adjust the flow speed in an air flow L in the flow receptacle 20 according to the adjustment of the vacuum strength. The steel tube of the flow receptacle 20 itself therefore has a first opening 21 for the connection of the adapter 24, a second opening 22 for the vacuum intake of the air stream L, wherein the first and second openings 21, 22 are oriented along the longitudinal axis A of the steel tube and/or have cross-sections which are perpendicular to the longitudinal axis X. Approximately in the center of the steel tube, the same has a socket 25 as a connector to a third opening 23 of the flow receptacle 20; the lambda probe 10 can be bolted onto the socket 25, for example via a bolt 26 or the like. The lambda probe 10 itself can further be connected to an ECU 40 of the vehicle via its wiring harness 11, particularly a water vehicle or land vehicle in the form of a commercial vehicle.

Even though the flow receptacle 20 in the present case has only one single socket 25 for receiving a single lambda probe 10, in one variant of the same, it is possible to realize a flow receptacle to which two or more lambda probes are intended to be attached. In the present case, a steel tube meets the specification overall as the receiver for one or more lambda probes. It is possible to install such a steel tube to a conventional vacuum cleaner 30, as explained, by means of the adapter 24. The detection of probe signals S of the lambda probe 10 can be realized via the wiring harness 11 to the ECU 40 of the engine. The same also has conventional diagnostic software for the purpose of calibrating the lambda probe 10. Following activation of the diagnostic software and activation of the vacuum cleaner 30, a calibration and simultaneous operational test measurement of the lambda probe 10 can occur.

It has also been proven successful over time to include an additional software module in the diagnostic software which is capable of representing not only a calibration value but also a heating current of the lambda probe 10. In particular, a representation which is a function of time has proven successful.

The heating current has proven advantageous in two respects. First, it is possible for the flow speed of the air stream L in the flow receptacle 20 to be indicated by said heating current. If, as explained above, this [speed] is too low, there is a risk of the oxidation of $N_2$ or $O_2$ from the surrounding air. If the flow speed is too high, there is a risk of the sensor cooling off by the transfer of heat to the air. The flow speed of the air stream L can be adjusted in a simple manner by means of controllers 32 on the vacuum cleaner 30, such that it is possible to provide the correct boundary conditions for a calibration at any time by observing the heating current.

Moreover, an operational test measurement of the lambda probe 10 is possible by means of the device 100 shown here, said measurement conforming to specifications, while at the same time, the device achieves the separation of this measurement from engine effects. As such, it is possible to reliably determine the calibration factor of a calibration value as an important criterion in both the development of engines and also in the customer service industry and/or in field applications.

In the field of engine development, there is the advantage that a reference system and analysis tool is made available via the device, and it is now possible to investigate and compare probes wherein the behavior thereof was previously unknown. In addition, first operational startups or other development uses in the field can be contemplated due to the present device 100. The detected values can be immediately compared to earlier results obtained at the development test bench. The device 100 therefore requires no additional electronics, because the evaluation runs via the motor ECU 40 and the wiring harness 11. The signal representation takes place by means of the diagnosis software on the part of the development engineer and/or the customer, or the customer service employee. A calibration module of the software can be extended with a module for representing the heating current and the calibration value in a comparatively simple manner.

Figure 2:
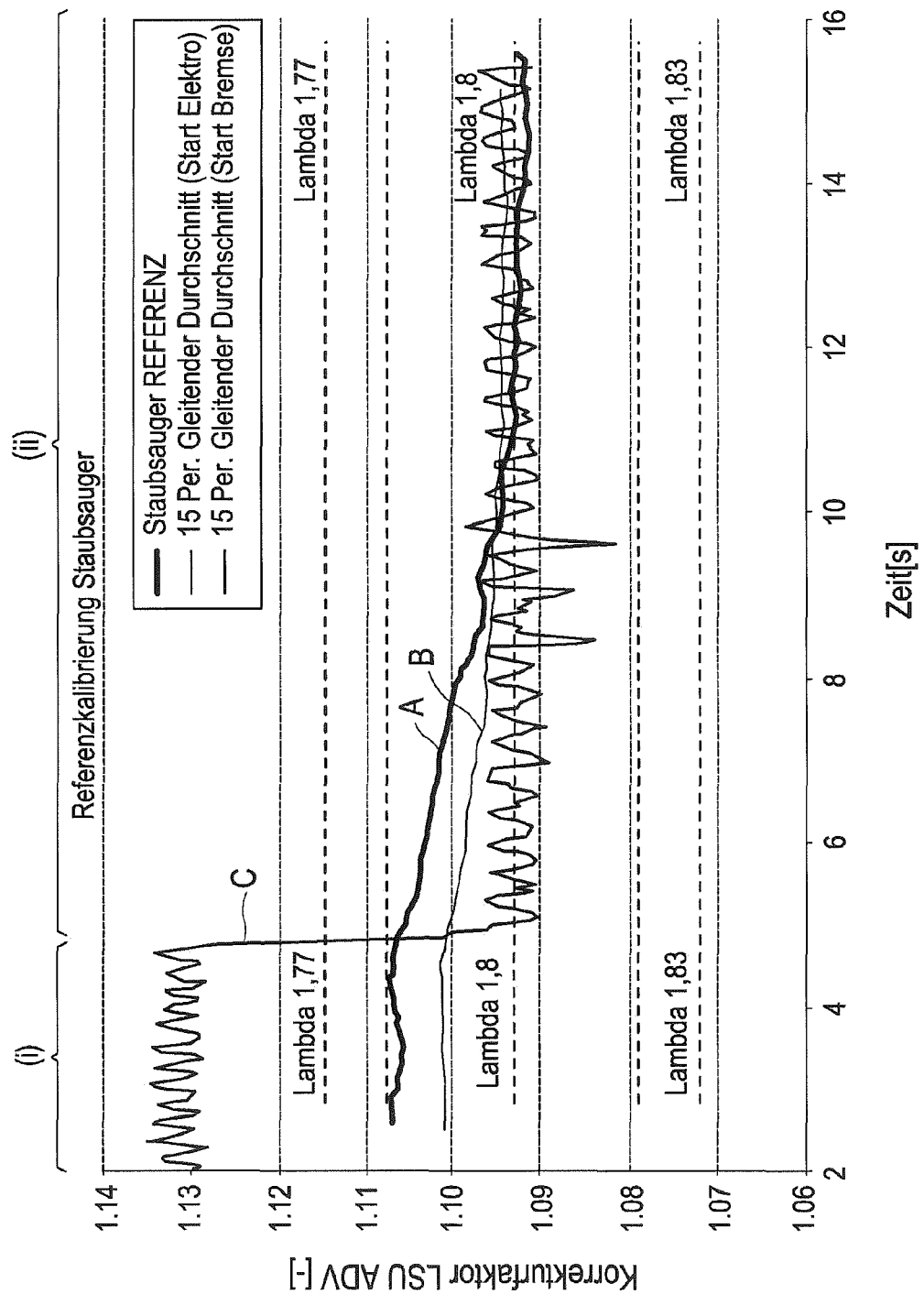
FIG. 2 shows an exemplary measurement result of a calibration device according to the concept of the disclosure compared to a calibration of a lambda probe carried out by the engine.

FIG. 2 also shows an exemplary illustration of a summary of correction factors over time, as determined by such diagnosis software. The correction factors according to curves A and B were determined for the case of a lambda probe connected, as always, to the engine construction. As is seen in curve A—with continuing operation of the electronics of the engine—and in curve B—with continuing operation of the brake of the engine—the primary contrast values of the curves A, B for determining the correction factor are comparatively poor. The relevance of such correction factors is not only limited, but also the determination thereof requires a longer time of potentially up to one minute or more. In contrast, curve C of the correction factor shows the operational test measurement of a lambda probe by means of a device described in FIG. 1. It is immediately clear that the difference between the air stream in region (ii), said air stream being switched on, and the stationary air in region (i) is significant. In addition, the correction factor when the air stream L is switched on and at approximately $\lambda=1.8$ is virtually immediately detected. The contrast value of such a calibration is significantly improved compared to the curves A, B. The result can also be called up virtually instantaneously because all engine effects are excluded in the determination of the correction factor as a calibration value. Overall, FIG. 2 therefore shows the superior validity and availability as a function of time of an operational test measurement of a lambda probe according to the concept of the disclosure.

The invention claimed is:

1. A method for the operational test measurement of a lambda probe for calibrating and/or determining the status of the lambda probe, wherein pure air is circulated around a probe head of the lambda probe, comprising:
   insertion of the lambda probe into a flow receptacle which is separate from an engine construction, and the flow receptacle is configured to circulate an air stream of ambient air around a probe head of the lambda probe;
   generation of the air stream in the flow receptacle; wherein the air stream of ambient air in the flow receptacle is generated by:
   attaching the flow receptacle to a vacuum device; and
   activating the vacuum device such that the air stream circulates around the probe head;
   evaluation of at least one probe measurement signal, wherein:
   a calibration value is obtained and a heating current of the lambda probe is evaluated, wherein for the purpose of evaluating the heating current, a heating current experience range is obtained and a determination is made as to whether the measured heating current is in the heating current experience range.

2. The method according to claim 1, wherein prior to the generation of the air stream, the following step is carried out:
   supplying of current to the probe and detection of probe measurement signals (S).

3. The method according to claim 1, wherein the heating current of the lambda probe is used for the purpose of determining the status of the lambda probe.

4. The method according to claim 1, wherein the probe signals are fed via a wiring harness and/or detected via an engine control unit connected to the same, and evaluated.

5. The method according to claim 1, wherein the vacuum device is a vacuum cleaner.

6. The method according to claim 1, wherein the flow receptacle is designed in the form of a tube.

7. The method according to claim 1, wherein a heating current of the lambda probe is used as an indicator for an adequate flow speed during the calibration.

8. The method according to one of the claim 1, wherein a heating current of the lambda probe is used as an indicator for a malfunction of the lambda probe.

9. A device for carrying out a method for an operational test measurement of a lambda probe, wherein pure air can be circulated around a probe head of the lambda probe, comprising:
   a flow receptacle with a socket for receiving the lambda probe, and the flow receptacle is configured to circulate an air stream of ambient air around the probe head;
   an evaluation unit for evaluating probe measurement signals; and
   a vacuum device which can be attached to the flow receptacle for generating the air stream of ambient air in the flow receptacle, wherein the vacuum device is designed in the form of a vacuum cleaner, and
   wherein the flow receptacle is separated from an engine; and
   wherein the evaluation unit is designed to evaluate a heating current of the lambda probe, wherein for the purpose of evaluating the heating current, a heating current experience range can be obtained, and it can be determined whether the measured heating current is in the heating current experience range.

10. The device according to claim 9, wherein the flow receptacle is designed in the form of a cylindrical tube, particularly a steel tube.

11. The device according to claim 9, wherein the evaluation unit has a software module for the purpose of representing a calibration value and/or the heating current, particularly as a function of time.

12. The device according to claim 9, wherein the flow receptacle is connected to a vacuum socket of the vacuum cleaner via a flexible adapter.

13. The device according to claim 9, wherein the evaluation unit is connected to the lambda probe via a wiring harness and/or an engine control unit connected thereto.

14. A system having a device according to claim 9 comprising a lambda probe that is , a wide-band lambda probe.

* * * * *